United States Patent [19]

Taguchi et al.

[11] 4,026,954

[45] May 31, 1977

[54] METHOD FOR PREPARING HEXYN-3-OL-1

[75] Inventors: Kenichi Taguchi, Tokorozawa; Akira Yamamoto; Toshinobu Ishihara, both of Niigata, all of Japan

[73] Assignee: Shin-Etsu Chemical Company Limited, Tokyo, Japan

[22] Filed: May 24, 1976

[21] Appl. No.: 688,976

[30] Foreign Application Priority Data

May 26, 1975 Japan .............................. 50-62624

[52] U.S. Cl. ..................... 260/632 B; 260/642 R; 260/665 G
[51] Int. Cl.² ........................................ C07C 29/00
[58] Field of Search ................ 260/665 G, 632 B

[56] References Cited

UNITED STATES PATENTS

| | | | |
|---|---|---|---|
| 1,963,935 | 6/1934 | Carothers et al. | 260/632 B |
| 3,663,591 | 5/1972 | Osbond et al. | 260/638 Y |
| 3,825,607 | 7/1974 | Descoins et al. | 260/632 B |

*Primary Examiner*—Joseph E. Evans
*Attorney, Agent, or Firm*—Toren, McGeady and Stanger

[57] ABSTRACT

Hexyn-3-ol-1 is prepared by the steps of (1) reaction of a methyl magnesium halide with propargyl chloride to form an ethylacetylene magnesium halide, (2) addition reaction of ethylene oxide to the ethylacetylene magnesium halide to form a halogen magnesium salt of hexyn-3-ol-1, and (3) hydrolysis of the halogeno magnesium salt of hexyn-3-ol-1.

10 Claims, No Drawings

METHOD FOR PREPARING HEXYN-3-OL-1

BACKGROUND OF THE INVENTION

This invention relates to a novel method for preparing hexyn-3-ol-1. Particularly, the invention relates to an industrially economical method for preparing hexyn-3-ol-1.

Hexyn-3-ol-1, which is a valuable intermediate for the production of cis-hexen-3-ol-1, is conventionally prepared by either of the following reactions. One is a reaction between ethylene oxide and sodium salt of ethylacetylene which is derived from acetylene through the following reaction sequence as disclosed in the Journel of Chemical Society, 1950, page 877.

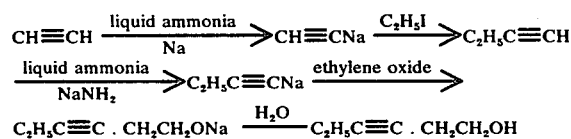

From the industrial point of view, this reaction has the disadvantages, such as, lengthy sequence of unit reactions, requirement of a pressure vessel owing to use of liquid ammonia (boiling point $-33°$ C) as a solvent, and low yeild, say, 50% or less of the product.

Further, the other reaction is the following reaction as disclosed in Japanese Patent Disclosure No. 18406/1975.

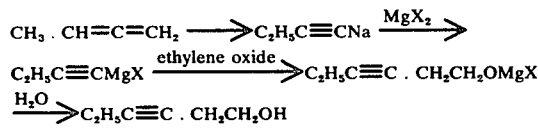

(X represents a halogen atom.)

According to this second reaction, 1,2-butadiene is a starting material which is converted in sequence into butynyl sodium, a butynyl magnesium halide and a halogenomagnesium salt of hexyn-3-ol-1, the last intermediate being hydrolyzed in the final reaction step to form hexyn-3-ol-1. However, it is disadvantaged in practice that the starting 1,2-butadiene is very expensive and the reaction for preparing th ethylacetylene magnesium halide requires tediously a long duration of stirring, say, 5 to 7 hours at a high temperature ranging from 50° to 120° C.

SUMMARY OF THE INVENTION

It is an object of this invention to provide a method for preparing hexyn-3-ol-1 in a higher yield and at a lower cost of production.

It is another object of this invention to provide a method for preparing hexyn-3-ol-1 involving reactions which are carried out in a shorter sequence and a lower temperature with unit procedures being simpler.

In accordance with the method of the invention, hexyn-3-ol-1, the useful intermediate in the production of cis-hexen-3-ol-1, is prepared by the method wherein propagyl chloride as the starting material, which is derived from propagyl alcohol, is reacted with a methyl magnesium halide (a Grignard reagent) to form an ethylacetylene magnesium halide and then subjecting the thus formed ethylacetylene magnesium halide to addition reaction with ethylene oxide to form a halogenomagnesium salt of hexyn-3-ol-1, which is finally hydrolyzed to form the desired product.

DETAILED DESCRIPTION OF THE PREFERRED EMBODIMENTS

The method of this invention for preparing hexyn-3-ol-1 proposes to obtain the product in higher yields as compared to any of the conventional methods and, accordingly, with much lower cost. Further the proposed process is a simplified process for preparing hexyn-3-ol-1 starting from propargyl chloride.

Those skilled in the art may synthesize hexyn-3-ol-1 which is a useful intermediate compound easily convertible into cis-hexen-3-ol-1, the socalled leaf alcohol, having superior green note by subjecting to partial hydrogenation using a Lindlar catalyst. However, no commercially profitable method has been proposed for the purpose.

The inventors of the present invention have made investigations to provide an advantageous method for preparing hexyn-3-ol-1 and have discovered a novel process using propargyl chloride as the starting material without the disadvantages as have been existent in the conventional methods. The method for preparing hexyn-3-ol-1 according to the present invention comprises the following reaction steps.

1. Reaction of two moles of methyl magnesium halide with one mole of propargyl chloride to form an ethylacetylene magnesium halide.
2. Addition reaction of the ethylacetylene magnesium halide to ethylene oxide to form a halogeno magnesium salt of hexyn-3-ol-1.
3. Hydrolysis of the halogeno magnesium salt of hexyn-3-ol-1.

Propagyl chloride to be used as the starting material in the present method can be obtained by chlorination of propargyl alcohol derived from acetylene and formaldehyde with ease and at a low cost. Therefore, hexyn-3-ol-1 is prepared more economically by the present invention than by either of the aforedescribed conventional methods.

The methyl magnesium halides used in the reaction with propargyl chloride include methyl magnesium chloride, methyl magnesium bromide and methyl magnesium iodide.

The method for preparing hexyn-3-ol-1 according to the present invention is shown by the following reaction.

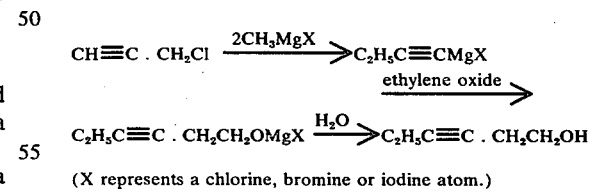

(X represents a chlorine, bromine or iodine atom.)

In the first reaction step, a methyl magnesium halide is prepared by reacting a methyl halide with metallic magnesium in an organic solvent, such as, anhydrous tetrahydrofuran or in a mixed solvent consisting of tetrahydrofuran and an inert solvent, such as, benzene, toluene, xylene or n-hexane in the conventional manner, then propargyl chloride is added to the mixture to react with the methyl magnesium halide to form a ethylacetylene magnesium halide. In this reaction, 2.0 to 2.5 moles of the methyl magnesium halide should be used per mole of propargyl chloride. The reaction should be continued for 0.5 to 5 hours within a temperature range from −50° to +60° C, preferably from −30° to +20° C with sirring. Any catalyst, such as copper (I) chloride, may be used in order to accelerate the reaction in a catalytic amount, for example, from 0.1 to 10 grams per mole of the methyl magnesium halide.

The second step is the reaction of ethylene oxide with the above-obtained ethylacetylene magnesium halide to form a halogeno-magnesium salt of hexyn-3-ol-1. The amount of the ethylene oxide used in this reaction is from 0.5 to 1 mole per mole of the methyl magnesium halide used in the preceding step. The reaction temperature should be kept between −10° C and +40° C.

The third step is the hydrolysis of the halogenomagnesium salt of hexyn-3-ol-1 to form the desired product. In this step it is preferred to drop the reaction solution into an aqueous ammonium chloride solution. The ultimate product, hexyn-3-ol-1, is obtained by distillating the organic phase separated from the aqueous phase after hydrolysis.

The method for preparing hexyn-3-ol-1 according to the present invention has again several advantages. The method proposes to use less expensive raw materials and carry out reactions at lower temperatures and in shorter periods of time compared to the conventional methods. Every reaction step according to the method is carried out at room temperature or in lukeward state (sometimes in chilled state) in a short time. Moreover, the desired product can be obtained in high yields. Thus, it may be concluded that the method for the preparation of hexyn-3-ol-1 according to the present invention is very economical.

The following examples are to further illustrate the invention, but not to be understood to limit the scope of the invention.

EXAMPLE 1

Into a 500-ml four-necked flask equipped with a stirrer, a thermometer, a dropping funnel and a reflux condenser connected to a dehumidifying tube packed with anhydrous calcium chloride at the terminal thereof, were charged 200 ml of anhydrous tetrahydrofuran, 10.6 g (0.44 mole) of metallic magnesium and a few pieces of iodine. Into the reaction mixture in the flask was introduced 0.48 mole of methyl chloride, and a methyl magnesium chloride complex was formed. 0.1 g of copper (I) chloride was added to the solution in the flask, and then 13.4 g (0.18 mole) of propargyl chloride was slowly dropped into the flask while the solution was stirred, keeping its temperature at 0° C. After the end of the dropping, stirring was continued at the same temperature for 2 hours, followed by further stirring at 30° C for 30 minutes, to complete the reaction. Thus, a solution of ethylacetylene magnesium chloride was obtained.

Following the above, 12 g of ethylene oxide kept at 0° C was dropped into the above solution of ethylacetylene magnesium chloride, and the solution was stirred for 4 hours after the end of the dropping of ethylene oxide at room temperature to obtain a solution of chloromagnesium salt of hexyn-3-ol-1. Thereafter, the above reaction solution was added to 200 g of 13% by weight aqueous ammonium chloride solution for the purpose of hydrolysis. The organic phase was separated from the aqueous phase, taken out, washed with water, dried and distilled to produce hexyn-3-ol-1 having a boiling point of 80° C (at 40 mmHg) in a yield of 62% based on the propargyl chloride.

EXAMPLE 2

Hexyn-3-ol-1 was prepared in an yield of 60% in the same manner as in Example 1 except that 0.48 mole of methyl bromide instead of methyl chloride was dropped into the reaction mixture, thus forming ethylacetylene magnesium bromide in the solution. The succeeding unit procedures, namely, the reaction with ethylene oxide, hydrolysis and distillation were all the same as in Example 1.

EXAMPLE 3

Hexyn-3-ol-1 was prepared in an yield of 54% in the same manner as in Example 1 except that 0.48 mole of methyl iodide instead of methyl chloride was dropped into the reaction vessel, thus giving ethylacetylene magnesium iodide in the solution. The succeeding unit procedures, namely, the reaction with ethylene oxide, hydrolysis and distillation were all the same as in Example 1.

EXAMPLE 4

Hexyn-3-ol-1 was prepared in an yield of 60% in the same manner as in Example 1 except that the temperature was kept at +10° C instead of 0° C while propargyl chloride was dropped into the solution of methyl magnesium chloride containing copper (I) chloride and that stirring was continued for one hour at +10° C after the end of dropping of propargyl chloride.

What is claimed is:
1. A method for preparing hexyn-3-ol-1 comprising the steps of;
    1. reaction of a methyl magnesium halide with propargyl chloride, to form an ethylacetylene magnesium halide,
    2. addition reaction of the ethylacetylene magnesium halide with ethylene exide, to form a halogenomagnesium salt of hexyn-3-ol-1, and
    3. hydrolysis of the haloganomagnesium salt of hexyn-3-ol-1.
2. The method for preparing hexyn-3-ol-1 as claimed in claim 1, in which said methyl magnesium halide is a member selected from the group consisting of methyl magnesium chloride, methyl magnesium bromide and methyl magnesium iodide.
3. The method for preparing hexyn-3-ol-1 as clamed in claim 1, in which the molar ratio of said methyl magnesium halide to said propargyl chloride in step (1) is from 2.0 to 2.5.
4. The method for preparing hexyn-3-ol-1 as claimed in claim 1, in which step (1) is carried out at a temperature between −50° C and +60° C.
5. The method for preparing hexyn-3-ol-1 as claimed in claim 1, in which step (1 ) is carried out at a temperature between −30° C and +20° C.
6. The method for preparing hexyn-3-ol-1 as claimed in claim 1, in which step (1) is carried out in the presence of a catalytic amount of copper (I) chloride.
7. The method for preparing hexyn-3-ol-1 as claimed in claim 6, in which said catalytic amount is from 0.1 to 10 g of copper (I) chloride per mole of said methyl magnesium halide.
8. The method for preparing hexyn-3-ol-1 as claimed in claim 1, in which step (3) is carried out by adding the reaction mixture containing said halogenomagnesium salt of hexyn-3-ol-1 to an aqueous solution of ammonium chloride.

9. The method for preparing hexyn-3-ol-1 as claimed in claim 1, in which the molar ratio of said ethylene oxide to said ethylacetylene magnesium halide in step (2) is from 0.5 to 1.

10. The method for preparing hexyn-3-ol-1 as claimed in claim 1, in which step (2) is carried out at a temperature between −10° C and +40° C.

* * * * *